United States Patent [19]

Yamato

[11] Patent Number: 4,826,850

[45] Date of Patent: May 2, 1989

[54] QUINOLINE BASE COMPOUND, PROCESS FOR THE PREPARATION THEREOF AND ANTICANCER AGENT CONTAINING THE SAME AS PHARMACOLOGICALLY EFFICACIOUS COMPONENT

[75] Inventor: Masatoshi Yamato, Okayama, Japan

[73] Assignee: Mect Corporation, Japan

[21] Appl. No.: 110,222

[22] Filed: Oct. 19, 1987

[30] Foreign Application Priority Data

Oct. 17, 1986 [JP] Japan .................. 61-246776

[51] Int. Cl.$^4$ ............... C07D 221/04; C07D 491/048; C07D 495/04; A61K 31/47
[52] U.S. Cl. .................................. 514/284; 514/285; 546/61; 546/62
[58] Field of Search ................ 546/62, 61; 514/285, 514/284

[56] References Cited

PUBLICATIONS

Dzieworski et al., Chem. Abstracts, vol. 59 (1963), entry 11365d.
G. J. Atwell et al., Journal of Medicinal Chemistry, 1972, vol. 15, No. 6, pp. 611-615.
Bruce F. Cain et al., Journal of Medicinal Chemistry, 1974, vol. 17, No. 9, pp. 922-930.
Bruce F. Cain et al., Journal of Medicinal Chemistry, 1975, vol. 18, No. 11, pp. 1110-1117.
David A. Van Echo et al., Cancer Research 39, 3881-3884, Oct. 1979.

Primary Examiner—Robert Gerstl
Assistant Examiner—Andrew G. Rozycki
Attorney, Agent, or Firm—Jacobs & Jacobs

[57] ABSTRACT

The present invention provides a quinoline base compound represented by the following general formula (1) of:

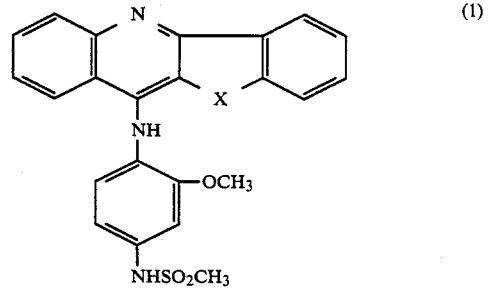

wherein X is $CH_2$, O or S. Further provided are the process for the preparation of the aforementioned quinoline base compound and an anticancer agent including the same as a pharmacologically efficacious component.

9 Claims, No Drawings

QUINOLINE BASE COMPOUND, PROCESS FOR THE PREPARATION THEREOF AND ANTICANCER AGENT CONTAINING THE SAME AS PHARMACOLOGICALLY EFFICACIOUS COMPONENT

BACKGROUND OF THE INVENTION

1. Field of the Invention

The present invention relates to novel quinoline base compounds, particularly benzofuranoquinoline base compounds, benzothienoquinoline base compounds and indenoquinoline base compounds, the process for the preparation thereof and anticancer agents containing the quinoline base compounds as pharmacologically efficacious components.

2. Description of the Related Art

In 1972, G. J. Atwell, B. F. Cain and R. N. Sealye synthesized acridine derivatives each having an amino group at position 9 of acridine, and found that some of them had the effect of inhibiting leukemia. (See "J. Med. Chem.", Vol. 15, 611 (1972).)

Cain et al. have investigated the interrelation between the anticancer effect of the acridine derivatives and the specific kind of alkylamino group at position 9 of acridine, and found that the most effective derivative is N-(4-(9-acridinylamino)-3-methoxyphenyl)-methanesulfoneamide (amsacrine). (See B. F. Cain, R. N. Seelye, G. J. Atwell, "J. Med. Chem.", Vol. 17, 922 (1974); and B. F. Cain, G. J. Atwell and W. A. Denny, "J. Med. Chem.", Vol. 18, 1110 (1975).)

Cain et al. have further reported that the compound obtained by reducing one of the two benzene rings constituting the skeletal structure of the amsacrine molecule, i.e. tetrahydroamsacrine, has reduced anticancer effect. (See B. F. Cain, R. N. Seelye, G. J. Atwell, "J. Med. Chem.", Vol. 17, 922 (1974).)

SUMMARY OF THE INVENTION

We have focussed our research on novel derivatives represented by the following general formula (1), particularly those having indenoquinoline, benzofuroquinoline or benzothienoquinoline in lieu of the acridine skeletal structure of amsacrine, and found that the derivatives have intensive anticancer activity. In view of such a finding, we have accomplished the present invention.

General Formula (1)

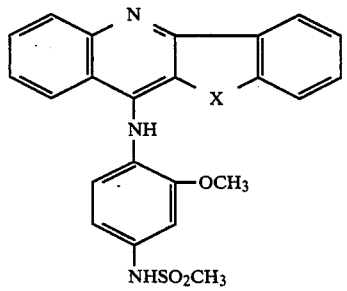

(1)

wherein X is $CH_2$, O or S.

The present invention is thus directed to the novel compounds represented by the general formula (1), and further provides a process for the preparation of an indenoquinoline, benzofuroquinoline or benzothienoquinoline base compound represented by the following general formula (4), (5) or (6) of:

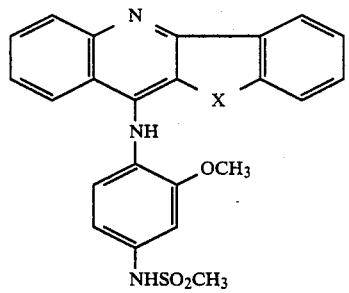

wherein X is O (Formula (4)), S (Formula (5)) or $CH_2$ (Formula (6)); which comprises the step of reacting a compound represented by the following general formula (2) of:

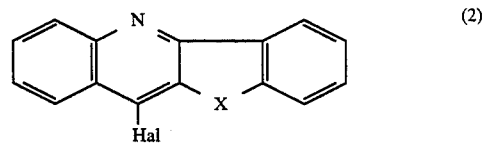

(2)

wherein X is the same as defined above, and Hal stands for a chlorine, bromine or fluorine atom; with N-(4-amino-3-methoxyphenyl)methanesulfoneamide which is represented by the following general formula (3) of:

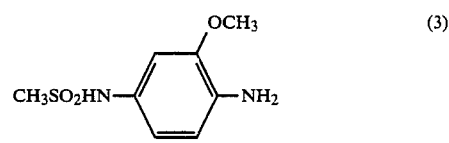

(3)

The present invention provides compounds of formula (1) and pharmaceutically acceptable salts thereof, such as the salts formed with methanesulfonic acid, phosphoric acid, lactic acid and the like, as well as the use of such compounds (1) and their pharmaceutically acceptable salts in the treatment of animals, including humans, suffering from cancer, such as leukemia, melanoma, cancer of the uterus and adenocarcinoma.

Accordingly, the present invention also provides a composition for treating an animal, including humans, suffering from cancer, which comprises an anti-cancer effective amount of a compound of formula (1) or a pharmaceutically acceptable salt thereof in combination with a pharmaceutically acceptable carrier or diluent therefor.

The present invention also provides a method for treating an animal, including humans, suffering from cancer, which comprises administering to the sufferer an anti-cancer effective amount of a compound of formula (1) or a pharmaceutically acceptable salt thereof.

The present invention will now be described in detail with reference to some examples thereof.

DESCRIPTION OF THE INVENTION (I) Preparation Scheme:

Initially, the process for the preparation of the compounds of this invention will be specifically described by referring to the preparation scheme.

(A) Synthesis of Indenoquinoline Base Compound:

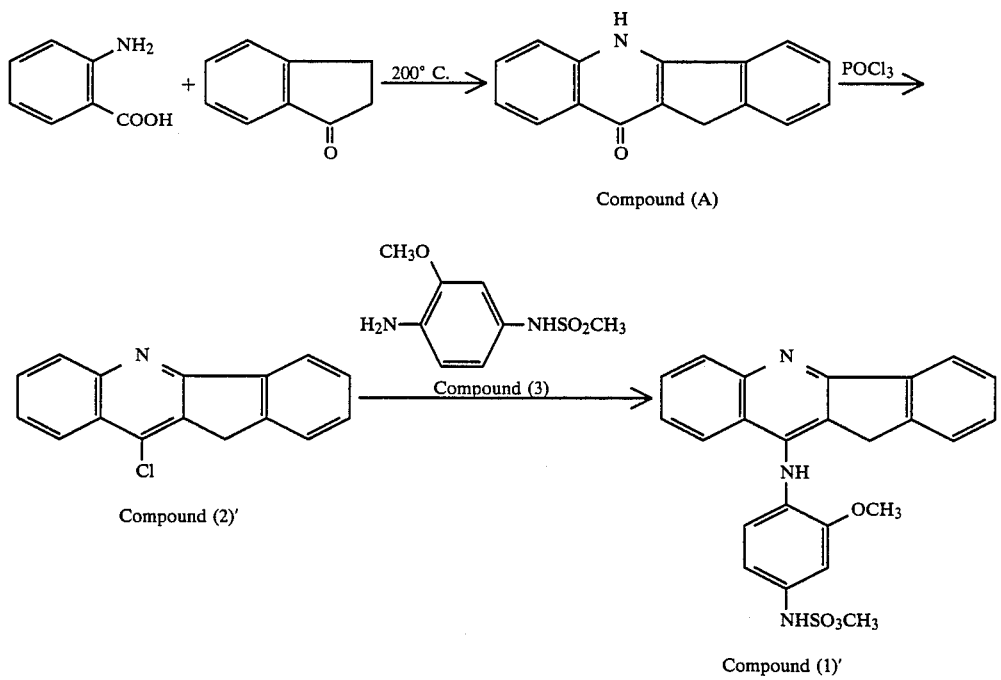

Compound (A)

Compound (2)'

Compound (1)'

(i) Preparation of Compound (2)':

A known Compound (A) is reacted with $POCl_3$, under the reaction conditions as will be described hereinafter, to prepare a Compound (2)'. The Compound (A) which is used in this first step may be prepared through the method disclosed by J. Schoen and K. Bogdanowicy-Sywed, "Roczniki Chem", Vol. 30, page 425 (1964).

In this step, it is not essential to use a catalyst and/or solvent. The reaction temperature ranges generally from about 100° C. to about 200° C., preferably from about 200° C. The reaction may be carried out generally for about 0.5 to about 3 hours, preferably for about 2 hours, under reflux by heating.

The reaction product is rinsed with pyridine and ether, followed by purification through a known method, to obtain Compound (A).

Using the Compound (A) as the starting material, a Compound (2)' is prepared generally in accordance with the method disclosed by N. H. Cromwell, R. A. Misch, "Journal of Organic Chemistry", Vol. 26, page 3812 (1961).

As a catalyst used in this step, concentrated sulfuric acid and hydrogen trifluoride-etherate ($BF_3$—$Et_2O$) may be used, the preferred catalyst being concentrated sulfuric acid. No solvent is used in this step.

The reaction temperature ranges generally from 50° C. to 106° C., and the reaction is carried out preferably at 106° C., which is the boiling point of the phosphorus oxychloride. The reaction may be continued for a period of 0.5 to 3 hours, preferably for 1.5 hours, under reflux by heating. Thus, the Compound (2)' can be prepared with good yields.

(ii) Preparation of Compound (1)':

The Compound (2)' is reacted with the Compound (3) under the reaction conditions described below to prepare a Compound (1)'.

Although triethylamine, pyridine or other catalysts may be used in this step, it is preferred that the reaction at this step proceed with no catalyst. Solvents which may be used in this step include ethoxyethanol and dimethylformamide, the preferred being ethoxyethanol.

The reaction may proceed at a temperature of from about 100° C. to about 135° C., preferably at about 135° C. The reaction may be continued for a period of 0.5 to 2 hours, preferably for about one hour, under reflux by heating. The resultant reaction solution is then processed through a known method to purify the reaction product, whereby a Compound (1)' is obtained.

(B) Synthesis of Benzofuranoquinoline Base Compound: N-(4-((benzofuro(3,2-b)quinoline-11yl)amino)-3-methoxyphenyl)methane sulfoneamide—Compound (4)

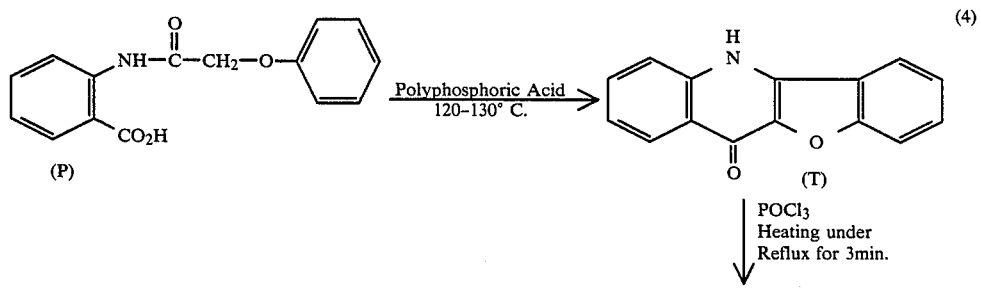

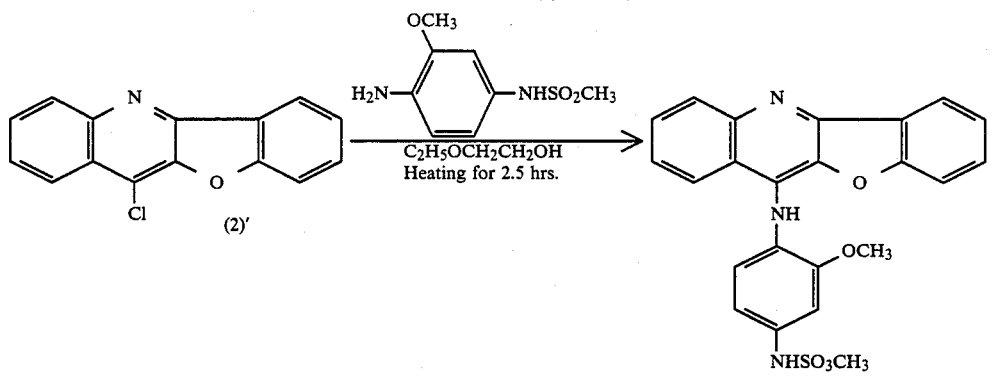

The steps for preparing a Compound (2)' from a starting material (P) through an intermediate compound (T) may be conducted following the method disclosed by S. Sunder and N. P. Peet, "J. Hetrocyclic Chem.", 15, 1379 (1978).

587 mg of the thus obtained Compound (2)' and 500 mg of N-(4-amino-3-methoxyphenyl)methanesulfoneamide were mixed in 5 ml of 2-ethoxyethanol, and the mixture was agitated for 2.5 hours under reflux by heating. After cooling the reaction solution and then adding a 10% aqueous solution of potassium hydroxide so that the solution is made to be alkaline, the reaction product was extracted by the use of chloroform. The chloroform phase was rinsed with water, dried, and then the solvent was distilled off. The residue was purified by passing it through an alumina column chromatogram, whereby 480 mg (Yield: 48%) of the objective compound (Compound (4)) was obtained.

Melting Point: 230° C.

Result of Ultimate Analysis: C, 63.62; H, 4.40; N, 6.46.

IR$_{max}^{Nujol}$ cm$^{-1}$: 3250, 3410.

$^1$H-NMR(CDCl$_3$+DMSO-d$_6$): δ: 3.00 (3H, S), 3.83 (3H, S), 6.74–7.24 (3H, m) 7.24–8.00 (6H, m), 8.12–8.58 (3H, m) 9.34–9.62 (1H, br.).

MS m/l: 433 (M+).

(C) Synthesis of Benzothienoquinoline Base Compound: N-(4-((benzothieno(3,2-b)quinoline-11-yl)amino)-3-methoxyphenyl)methanesulfoneamide—Compound (5)

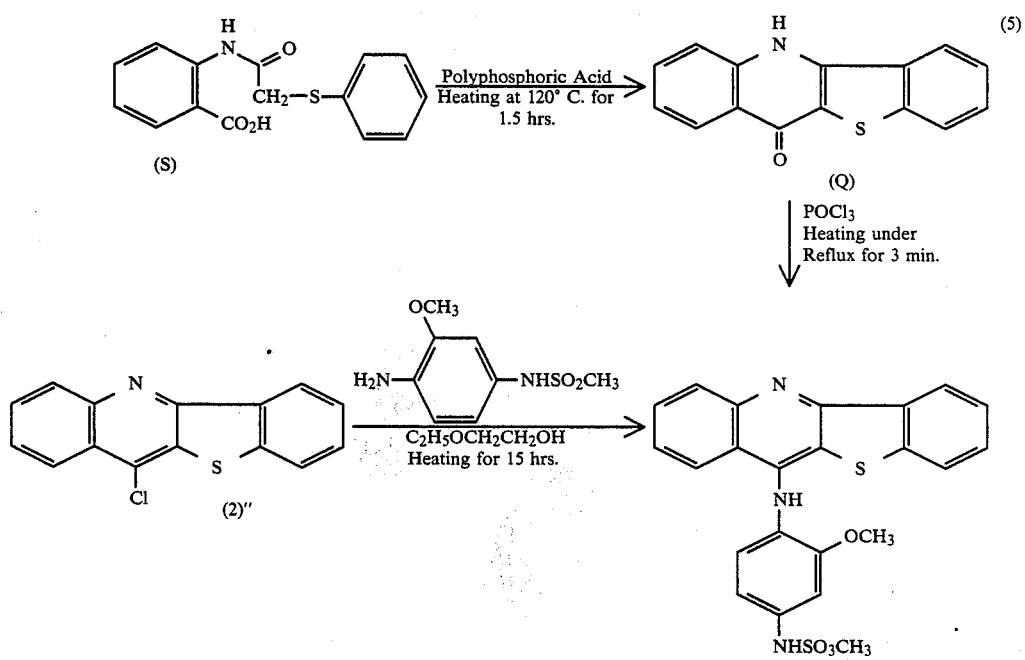

The steps for preparing a compound (2)' from a starting material (S) through an intermediate product (Q) were carried out generally following the process disclosed by K. Gorlitzer and J. Weber, "Arch Pharm.", 314, 76 (1980).

1.0 g of the thus obtained 11-chlorobenzothieno-(3,2-b)quinoline (Compound (2)') and 0.8 g of N-(4-amino-3-methoxyphenyl)methanesulfoneamide were dissolved in 15 ml of 2-ethoxyethanol, and the solution was agitated for 15 hours under reflux by heating. After cooling the solution, the precipitated crystal was obtained by filteration and dissolved in a 10% potassium hydroxide solution, and then the product was extracted with chloroform. The chloroform layer was rinsed with water, dried, and then the solvent was distilled off. The residue was recrystallized from acetone, whereby 0.8 g (Yield: 48) of a Compound (5) was obtained.

Melting Point: 265° to 266.5° C. (Decomposed).

Result of Ultimate Analysis: C, 61.42; H, 4.35; N, 9.28.

$IR_{max}^{Nujol}$ cm$^{-1}$: 3230, 1330.

$^1$H-NMR (DMSO-d$_6$): δ: 3.13 (3H, S), 3.68 (3H, S), 6.87–8.82 (11H, m), 8.91–9.21 (1H, br.), 9.80–10.08 (1H, br.).

MS m/l: 449 (M+).

Preparation Example 1: (Intravenous Injection and Drip)

To each of the Compounds (4), (5) and (6) was added a 10% hydrochloric acid, and the thus formed solution was aseptically dispensed in vials so that each vial contained 120 mg of each of the Compounds (4), (5) and (6) and 0.36 ml of the 10% hydrochloric acid. The vials were then sealed for storage.

Immediately before use, 19.6 ml of a 0.85% physiological saline solution was added to the contents of each vial to form a preparation for intraveous injection.

The thus formed preparation was administered at a dose of 20 ml a day through intravenous injection or intravenous drip depending on the condition of the patient.

(II) Pharmacological Activity:

No toxicity has been observed when the compound of this invention is continuously administered to mice at a dose of 50 mg/kg. The compound of this invention may be administered orally in the form of a tablet, capsule or aerosol, or may be administered through intravenous or subcutaneous injection. The compound of this invention may also be administered through a non-oral route, for example, in the form of a preparation for intravenous drip or suppositories. Although the effective amount thereof is varied depending on the condition of the patient, the administration route, the specific type of preparation used and the cycle or administration times for the administration thereof, the effective amount thereof ranges generally from 0.1 to 80 mg/weight (kg), preferably from 10 to 50 mg/weight (kg) of the patient per day when it is administered to an adult patient through a non-oral route. The compound of this invention may also be used in the form of a preparation for injection or intravenous drip. Alternatively, it may be used in the form of a suspension, solution or emulsion in an oily or aqueous vehicle, and may be admixed with a suspension or emulsifier, a stabilizer or a dispersing agent.

Since the compound of this invention has excellent effects in prolonging the life of a patient and is low in toxicity, as described above, the compound of the invention may be used to deal with cancer effectively.

The present invention will now be described more specifically with reference to Examples.

Example 1: (Preparation of Compound (1))

A mixture of anthranilic acid (0.5 g, 3.65 mmol) and 1-indanone (0.72 g, 5.45 mmol) was prepared and heated, under agitation, to 200° C. for 1.5 hours. After cooling, the reaction mixture was rinsed with pyridine and ether to obtain a Compound (A) in the form of a crystal having a melting point of 363° to 364° C. Yield was 0.5 g (56%).

Concentrated sulfuric acid (one drop) and phosphorus oxychloride (6 ml) was added to the compound (A) (0.40 g, 1.72 mmol) to form an admixture which was heated for 2 hours under reflux. After completion of the reaction, the excess phosphorus oxychloride was distilled off to obtain a residue which was neutralized with concentrated aqueous ammonia, and then extracted with chloroform. The chloroform layer was rinsed with an aqueous solution of acid potassium carbonate and water, and then the chloroform was distilled off, whereby 0.43 g (Yield: 99%) of a Compound (2)' having a melting point of 162° to 163° C. was obtained. The thus obtained Compound (2)' (0.20 g, 0.80 mmol) and the Compound (3) (0.18 g, 0.83 mmol) were dissolved in ethoxyethanol to form a solution which was heated for an hour under reflux. The residue was rinsed with methanol and purified to obtain 0.24 g (Yield: 70%) of a Compound (1) having a melting point of 245° to 250° C.

Result of Ultimate Analysis (as $C_{24}H_{22}N_3O_3S$): Cald.: C, 61.60; H, 4.74; N, 8.98; Found: C, 61.34; H, 4.68; N, 8.75.

$IR^{Nujol}$ cm$^{-1}$: 3410, 3240, 1320.

$^1$H-NMR (DMSO-d$_6$): δ: 3.18 (3H, S, CH$_3$SO$_2$), 3.61 (2H, S, CH$_2$), 3.78 (3H, S, CH$_3$O).

m/z: 431 (M+), 352 (M+-CH$_3$SO$_2$).

Preparation Example 1: (Injection, Intravenous Drip)

A 10% hydrochloric acid was added to the Compound (1), and the thus formed solution was aseptically dispensed in vials so that each vial contained 120 mg of the Compound (1) and 0.36 ml of the 10% hydrochloric acid. The vials were then sealed for storage.

Immediately before use, 19.6 ml of a 0.85% physiological saline solution was added to the contents of each vial to form a preparation for intravenous injection.

The thus formed preparation was administered at a dose of 20 ml a day through intravenous injection or intravenous drip depending on the condition of the patient.

Test Example 1: Test for Anti-tumor Effect (1) Effect in Inhibiting Growth of KB-Cells The KB-cell, one of the cancer-causing tumor cells, was incubated in an in vitro floating incubation system, and the pharmacological effects of the Compounds (4) and (5) were compared with a control to which the compounds had not been added.

System Used in Experiment:

Cells Used:

KB Cells (derived from a human epidermoid carcinoma of the mouth).

Culture Medium Used:

Eagles minimal essential medium (MEM)-10% calf serum.

Conditions of Incubation:

37° C. in a carbon dioxide gas incubator (5% CO$_2$).

Procedure in Experiment:

Day 0: The KB cells were diluted to $2 \times 10^4$/ml medium. 3 ml of the thus diluted KB cell suspension was incubated on a 60 mm plastic dish, at 2 dishes per dose level.

Day 1: Each drug was added into each dish so that the drug content in each dish was adjusted, respectively, to 100, 30, 10, 3 and 1 μg/ml.

Day 4: The cells were stripped from the surface of each dish, and the number of cells was counted using a Kohlter's counter.

Standard for Evaluation:

In general accordance with the stipulations of the National Cancer Institute (NCI), U.S.A., the concentration of each drug or compound which showed substantially 50% growth inhibition (ED$_{50}$), when compared to the control, was determined. A substance or drug having an ED$_{50}$ value of not more than 4 μg/ml for a synthesized product was appraised as an effective substance. Meanwhile, in evaluating the effect of inhibiting growth of KB-cells, the number of surviving cells was counted by a Kohlter's counter, and the counted number was compared to that of the control (without the addition of the Compound (1)) to find the concentration of the drug for inhibiting the growth by 50%, the thus found concentration being estimated as the ED$_{50}$ value. The results are shown below.

Results of Test for Anticancer Effect:
(1) Effect in Inhibiting Growth of KB-Cells

| Tested Compound No. | Concentration (μg/ml) | Inhibition Rate (%) |
|---|---|---|
| 4 | 0.3 | 50 |
| 5 | 0.3 | 50 |
| 6 | below 0.3 | 50 |
| Control | 0 | 0 |

Test Example 2: Effect in Prolonging the Life of Mouse with Cancer, and Acute Toxicity of Drugs Using P-388 mice with cancer, the pharmacological efficacy of the aforementioned compounds was evaluated by comparing with a control to which no such compound had been added.

System Used in Experiment:
Animal Used: CDF$_1$ Mice (6 mice/group)
Cancer (Tumor): P-388
Number of Incubated Cells: 10$^6$ cells/mouse
Incubated Site: i.p.
Days at which Drugs Were Administered: Days 1 and 5, or days 1 to 9
Quantities of Drugs Administered: When a drug was administered at days 1 and 5, the maximum dosed quantity was set at LD$_{50}$ or 400 mg/kg/day; and when a drug was administered at days 1 to 9, the maximum dosed quantity was set at ½×LD$_{50}$ or 200 mg/kg/day. The experiment was conducted with groups of mice being administered the respective drugs at 3 dose levels incuding the maximum level, ½ of the maximum level and ¼ of the maximum level.

Standard for Evaluation:
When the T/C %, i.e. the ratio of the survival time (days) of a treated group (administered with a certain drug) to the survival time of a control group (administered with no drug), was 120% or more for a synthesized substance and 130% or more for a natural substance, the drug was appraised as effective (P). The survival time of the group administered with no drug is normally about 10 days (median survival time). In the following Table, an indication of "T/C 0%" means that not less than three mice were dead due to toxicity within 5 days.

(2) Effect in Prolonging Life of P-388 Mice

| Tested Compound No. | Dosage (mg/kg) | Life Prolonging Rate (%) |
|---|---|---|
| 4 | 50 | 200 |
|   | 25 | 195 |
|   | 12.5 | 180 |
| 5 | 50 | 170 |
|   | 25 | 170 |
|   | 12.5 | 138 |
| 6 | 400 | 0 |
|   | 200 | 60 |
|   | 100 | 240 |
|   | 50 | 217 |
|   | 12.5 | 166 |
| Control | 0 | 100 |

What is claimed is:

1. A quinoline base compound represented by the following formula (1) of:

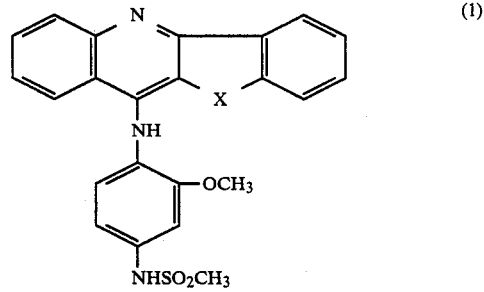

wherein X is CH$_2$, O or S, or a pharmaceutically acceptable salt thereof.

2. The compound according to claim 1, wherein X is CH$_2$.

3. The compound according to claim 1, wherein X is O.

4. The compound according to claim 1, wherein X is S.

5. A method of treating an animal, including humans, suffering from leukemia, melanoma, cancer of the uterus or adenocarcinoma, which comprises administering to the sufferer an effective amount of a compound according to claim 1 or a pharmaceutically acceptable salt thereof.

6. A composition for treating an animal, including humans, suffering from leukemia, melanoma, cancer of the uterus or adenocarcinoma, which comprises an effective amount of a compound according to claim 1 or a pharmaceutically acceptable salt thereof, in combination with a pharmaceutically acceptable carrier or diluent therefor.

7. The compound of claim 2 in the form of a lactic acid salt.

8. The compound according to claim 3 in the form of a methanesulfonic acid.

9. The compound according to claim 4 in the form of a phosphoric acid salt.

* * * * *